(12) United States Patent
Hwang et al.

(10) Patent No.: US 7,879,906 B2
(45) Date of Patent: Feb. 1, 2011

(54) GABA ANALOGS, COMPOSITIONS AND METHODS FOR MANUFACTURING THEREOF

(75) Inventors: Jenn-Tsang Hwang, Hsinchu (TW); Chrong-Shiong Hwang, Hsinchu (TW); Yow-Lone Chang, Hsinchu (TW); Chung-Niang Yao, Hsinchu (TW)

(73) Assignee: Anchen Laboratories, Inc., Irvine, CA (US)

( * ) Notice: Subject to any disclaimer, the term of this patent is extended or adjusted under 35 U.S.C. 154(b) by 534 days.

(21) Appl. No.: 11/943,983

(22) Filed: Nov. 21, 2007

(65) Prior Publication Data

US 2008/0125483 A1    May 29, 2008

Related U.S. Application Data

(60) Provisional application No. 60/867,130, filed on Nov. 24, 2006.

(51) Int. Cl.
*A01N 45/00* (2006.01)
*C07D 307/34* (2006.01)
*C07C 211/00* (2006.01)

(52) U.S. Cl. ............... 514/467; 549/261; 549/229; 564/463

(58) Field of Classification Search ............ 514/467; 549/261, 229; 564/463
See application file for complete search history.

(56) References Cited

U.S. PATENT DOCUMENTS

| 6,818,787 | B2 | 11/2004 | Gallop et al. |
| 6,972,341 | B2 | 12/2005 | Gallop et al. |
| 2004/0077553 | A1 | 4/2004 | Gallop et al. |
| 2006/0229361 | A1 | 10/2006 | Gallop et al. |
| 2007/0010453 | A1 | 1/2007 | Gallop et al. |

FOREIGN PATENT DOCUMENTS

| EP | 1902714 | 3/2008 |
| WO | WO 02/100347 | 12/2002 |

*Primary Examiner*—Janet L. Andres
*Assistant Examiner*—Raymond Covington
(74) *Attorney, Agent, or Firm*—Wood, Phillips, Katz, Clark & Mortimer

(57) ABSTRACT

The invention provides compounds of Formula (I), pharmaceutical compositions and methods of synthesis thereof.

(I)

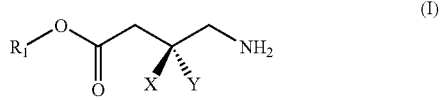

15 Claims, No Drawings

GABA ANALOGS, COMPOSITIONS AND METHODS FOR MANUFACTURING THEREOF

RELATED APPLICATIONS

This application claims the benefit of U.S. Provisional application 60/867,130, filed Nov. 24, 2006, the disclosure of which is incorporated by reference herein.

BACKGROUND OF THE INVENTION

Gamma aminobutyric acid ("GABA") is one of the major inhibitory neurotransmitters in the central nervous system of mammals. GABA regulates neuronal excitability through binding to specific membrane proteins (et al., $GABA_A$ receptor), which results in opening of an ion channel. Low levels of GABA have been observed in individuals suffering from epileptic seizures, motion disorders (e.g., multiple sclerosis, action tremors, tardive dyskinesia), panic, anxiety, depression, alcoholism and manic behavior. Therefore, it is of interest to develop GABA analogs, which have superior pharmaceutical properties in comparison to GABA.

A number of GABA analogs, with considerable pharmaceutical activity have been synthesized and described in the art (See, e.g., Satzinger et al., U.S. Pat. No. 4,024,175; Silverman et al., U.S. Pat. No. 5,563,175; Silverman et al., U.S. Pat. No. 6,028,214; Gallop et al. US 200400077553; Cundy, et al. U.S. Pat. No. 20050209319; Bryans, International Publication No. WO 00/31020; Bryans et al. WO 02/00209; Barret, et al. WO 05/027850; 04/089289). Among those synthesized GABA analogs, gabapentin, pregabalin, vigabatrin, and baclofen have been marketed and used to treat different disorder syndromes. For example, gabapentin and pregabalin are used to clinically treat, inter alia, epilepsy and neuropathic pain. The sales for gabapentin are higher than twenty millions.

One significant problem of the GABA analogs is the formation of toxic impurities such as gabapentin lactams during synthesis or formulating of GABA analogs. The amino group of GABA analogs can react with its carboxy functional group to form the gamma-lactam, which is more toxic than the GABA analog drug. For example, the toxicity of gabapentin ($LD_{50}$, mouse) is more than 8000 mg/kg, while the corresponding lactam has toxicity ($LD_{50}$, mouse) of 300 mg/kg. The high toxicity of the gamma-lactam structure results in serious difficulties in formulating GABA analogs and requires the addition of special purification steps to minimize the gamma-lactam contamination.

Rapid systemic clearance is another significant problem of many GABA analogs that are excreted by the kidney unmetabolized, thus requiring frequent dosing to maintain a therapeutic or prophylactic concentration in the systemic circulation (Bryans et al., Med. Res. Rev., 1999, 19, 149-177). For example, 300-600 mg of gabapentin single dose administered three times daily is typically used for anticonvulsive therapy. Higher doses (1800-3600 mg/day in divided doses) are typically used for the treatment of neuropathic pain states.

Employing a sustained release drug delivery system is a conventional solution to the problem of rapid systemic clearance of GABA analogs. However, the absorption efficiency in the colon and rectum for many GABA analogs, including gabapentin and pregabalin, is not as good as it is in the small intestine, where the GABA analogs are transported by the large neutral amino acid transporter ("LNAA") (Jezyk et al., Pharm. Res., 1999, 16, 519-526). A successful application of sustained release technologies for many GABA analogs has been limited accordingly.

Thus, there is a need to develop a new GABA analog or a prodrug thereof, which is well absorbed from all parts of the intestine and for which sustained release technologies are applicable in resolving the above problems.

SUMMARY OF THE INVENTION

Accordingly, the present invention provides novel GABA analogs, novel prodrugs of pregabalin pharmaceutical compositions and methods of synthesis thereof.

In one embodiment, the present invention provides compounds of Formula (I):

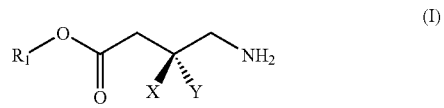

or pharmaceutically acceptable salts, hydrates or solvates thereof, wherein $R_1$ is

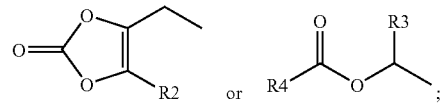

$R_2$ and $R_3$ are independently hydrogen or alkyl;

$R_4$ is $C_1$-$C_6$ alkyl group, $C_6$-$C_8$ aryl group or $C_1$-$C_6$ alkoxyl group; and X and Y are independently hydrogen, chlorophenyl, 2-methylpropyl, or benzyl, or optionally X and Y together with the carbon atom to which they are bonded form a cyclohexyl. In an alternative embodiment, the present invention provides pharmaceutical compositions comprising one or more compounds of the invention, together with a pharmaceutically acceptable carrier.

In an alternative embodiment, the present invention provides methods for treating or preventing epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. The methods generally involve administering to a patient in need of such treatment or prevention a therapeutically effective amount of a compound of the invention.

The compounds of the invention have a promoiety, which is typically non-toxic, attached to the amino group or carboxy group of GABA analogs, where the promoiety is designed to be cleaved by either enzymatic or chemical means to generate GABA analogs in vivo at a time following administration to a mammal of the compound of the present invention. It is expected that the compounds of the invention are metabolized into GABA analogs in vivo and may further behave as prodrugs of GABA analogs. It is further expected that the lipophillic nature of compounds of the invention could improve the colon and rectal absorption efficiency and the subsequent metabolism and release of the prodrugs or other compounds of the invention into the blood stream.

DETAILED DESCRIPTION OF THE INVENTION

Definitions:

"Alkyl" by itself, or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyl such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkoxy," by itself, or as part of another substituent, refers to a radical —OR where R represents an alkyl or cycloalkyl group, as defined herein. Representative examples include, but are not limited to, methoxy, ethoxy, propoxy, butoxy, cyclohexyloxy, and the like.

"Cycloalkyl," by itself, or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like.

"Aryl," by itself, or as part of another substituent, refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. Preferably, an aryl group comprises from 6 to 20 carbon atoms, more preferably between 6 to 8 carbon atoms.

"Pharmaceutically acceptable salt" refers to a salt of a compound of the invention, which is pharmaceutically acceptable and possesses the desired pharmacological activity of the compound of the invention. Such salts include, but are not limited to: (1) acid addition salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound of the invention is either replaced by a metal ion, e.g., an alkali metal ion, an alkaline earth ion, or an aluminum ion; or it conjugates with an organic base such as ethanolamine, diethanolamine, triethanolamine, N-methylglucamine, and the like. Pharmaceutically acceptable salts also include salts of the compounds present in vivo.

"Pharmaceutically acceptable hydrate" or "pharmaceutically acceptable solvate" refer correspondingly to a hydrate or solvate of a compound of the invention, which is pharmaceutically acceptable and possesses the pharmacological activity of the compound of the invention. Pharmaceutically acceptable hydrates or solvates also include hydrates or solvates of the compounds present in vivo.

"Prodrug" refers to a derivative of a drug molecule that requires a transformation within the body to release the active drug. Prodrugs are frequently (though not necessarily) pharmacologically inactive until converted to the active drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule, masks, reduces, or prevents reactivity of the functional group.

"Pharmaceutically acceptable carrier" refers to a diluent, adjuvant, excipient or carrier which is used in the administration of a compound of the invention.

"Compound of the invention" refers to a synthetically (i.e., ex vivo) prepared compound of the invention or to a compound of the invention produced in vivo after administration of a different compound of the invention.

Compounds of the Invention:

The compounds of the invention include compounds of Formula (I):

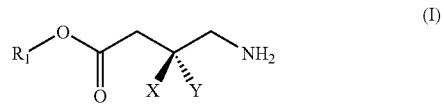

or pharmaceutically acceptable salts, hydrates or solvates thereof, wherein $R_1$ is

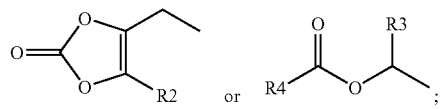

$R_2$ and $R_3$ are independently hydrogen or alkyl;

$R_4$ is $C_1$-$C_6$ alkyl group, $C_6$-$C_8$ aryl group or $C_1$-$C_6$ alkoxyl group; and X and Y are independently hydrogen, chlorophenyl, 2-methylpropyl, or benzyl, or optionally X and Y together with the carbon atom to which they are bonded to form a cyclohexyl.

In one embodiment, the compound of formula (I) is a compound of formula (II), (III) or (IV):

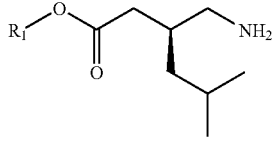
(II)

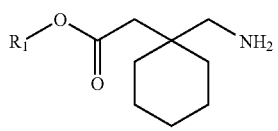
(III)

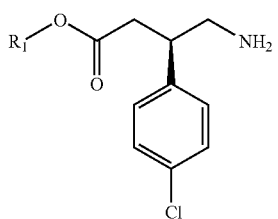
(IV)

or a pharmaceutically acceptable salt, hydrate or solvate thereof, wherein $R_1$ is

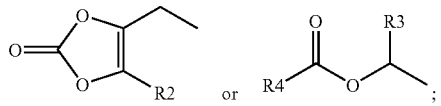

$R_2$ and $R_3$ are independently hydrogen or alkyl; and $R_4$ is $C_1$-$C_6$ alkyl group, $C_6$-$C_8$ aryl group or $C_1$-$C_6$ alkoxyl group.

In a preferred embodiment of formula (II), the compound of the invention is a compound of formula (V):

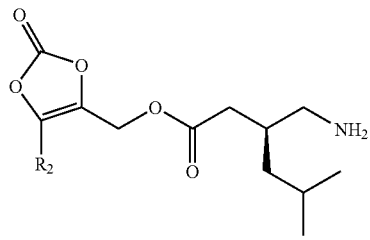
(V)

or a pharmaceutically acceptable salt, hydrate or solvate thereof, wherein $R_2$ is hydrogen or alkyl. In a most preferred embodiment, $R_2$ is methyl.

In another preferred embodiment of formula (II), the compound of the invention is a compound of formula (VI)

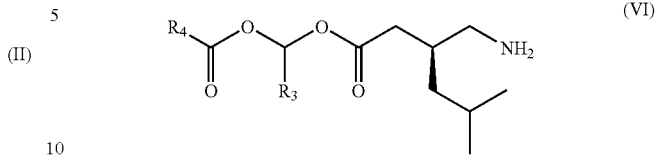
(VI)

or a pharmaceutically acceptable salt, hydrate or solvate thereof, wherein $R_3$ is hydrogen or alkyl; and $R_4$ is $C_1$-$C_6$ alkyl group, $C_6$-$C_8$ aryl group or $C_1$-$C_6$ alkoxyl group.

The compounds of the invention include prodrugs of pregabalin. It is expected, though not required, that the embodiments of these compounds of the invention will be metabolized into pregabalin through one or more of the following paths A or B following administration to a mammal.

The following path A illustrates that an embodiment of the compound of Formula (V) is metabolized into pregabalin when administered to a mammal.

Path A

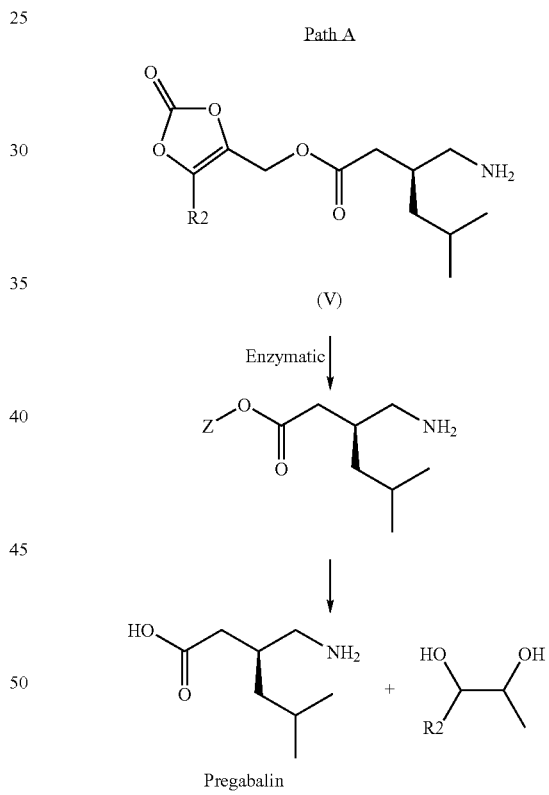

wherein Z is

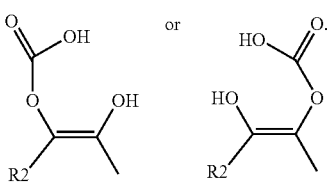

The following path B illustrates that an embodiment of the compound of Formula (VI) is metabolized into pregabalin when administered to a mammal

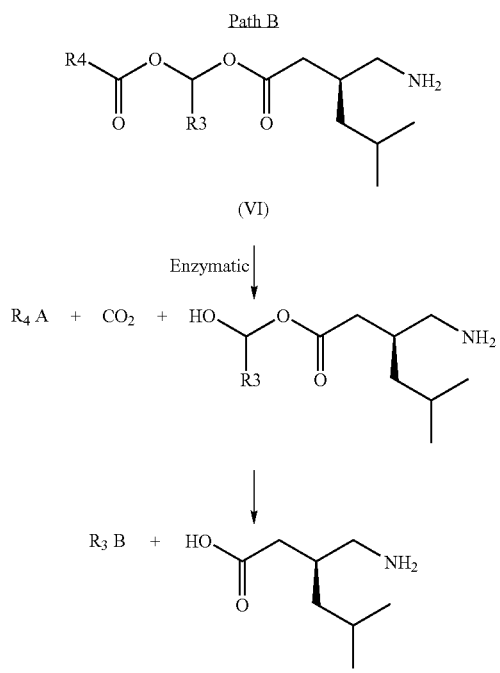

Wherein A and B are independently hydrogen, hydroxyl or other substituted groups.

It is expected that the lipophilic nature of the compounds of the invention could increase the absorption window from the small and large intestines by passive or carrier transport. Subsequently, the compounds of the invention are metabolized into pregabalin and released in the blood. In a preferred embodiment, it is further expected that the premoiety of the compounds of the invention could increase the level of protein-binding, increase volume of distribution, prolong duration of action, and/or reduce the dosing frequency.

Use of the Compounds of the Invention

In one embodiment, the compounds of the invention can further be used in combination with a pharmaceutically acceptable vehicle or carrier to provide a pharmaceutical formulation that is suitable for administration to a mammal. The pharmaceutical formulations of the invention comprise a compound of the invention and at least a pharmaceutically acceptable carrier. It can be in a dosage form of solutions, suspensions, emulsions, tablets, pellets, capsules, powders, sustained-release or delayed release formulations, suppositories, or any other form suitable for use. The pharmaceutical formulations of the invention can be manufactured by any conventional methods known in the art.

The compounds and/or formulations of the invention may be suitable for administration to a mammal for treatment or prevention of GABA relevant disorders, for example, epilepsy, neuropathic pain, postherapeutic neuralgia, restless legs syndrome, depression, anxiety, psychosis, cranial disorders, neurodegenerative disorders, pain, inflammatory disease, gastrointestinal disorders, etc. The in vivo effects of the active metabolites and compounds of the invention described herein may not be exerted by those compounds as such, but by one or more degradation products.

Suitable dose ranges for administration are dependent on the potency of the compounds of the invention or their active metabolites. Suitable doses generally range from about 0.001 mg to about 200 mg of a compound of the invention per kilogram body weight. The dose ranges may be readily determined by methods known to the skilled artisan.

Animal studies may be conducted to understand the pharmacokinetic or pharmacodynamic properties of the compounds of the invention. The design of animal studies may be determined by a skilled artisan.

Example 1

In order to understand the pharmacokinetic properties of the compounds of the invention, the compounds of the invention are prepared as a solution, with Tween 80 or PEG 400 used as solubilizer, and directly administered to rats at a pharmaceutically acceptable dose. Blood samples (0.5 ml) are collected at selected time points during 24 hours following dose administration. The blood samples are subjected to removal of macromolecular proteins and then analyzed with an LC/MS/MS spectrometer or by other analytical methods known in the art. The maximum plasma concentration ($C_{max}$), area under a curve (AUC), and half-life ($T_{1/2}$) of the compounds of the invention are then calculated by commercial software.

Example 2

Table 1 provides examples of the invention as illustrative embodiments, with non-limiting details given herein. Other embodiments and methods for synthesis of the compounds of the invention are either described in the art or will be readily apparent to the skilled artisan.

TABLE 1

| Code | Structure | Formula type/R2, R3, R4 | CLogP |
| --- | --- | --- | --- |
| Pregabalin | 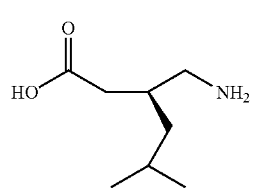 | | −0.915 |

TABLE 1-continued

| Code | Structure | Formula type/R2, R3, R4 | CLogP |
|---|---|---|---|
| PGB-02 | 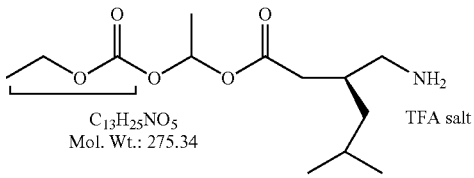 C₁₃H₂₅NO₅ Mol. Wt.: 275.34 TFA salt | Formula (II) 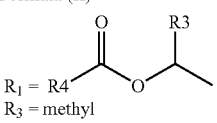 R₁ = R4 R₃ = methyl R₄ = ethoxyl | 2.4779 |
| PGB-03 | 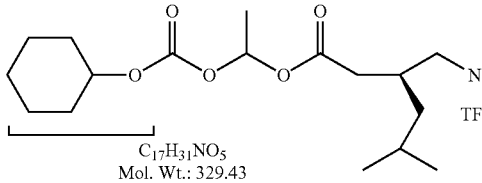 C₁₇H₃₁NO₅ Mol. Wt.: 329.43 TFA salt | Formula (II) 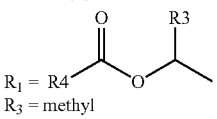 R₁ = R4 R₃ = methyl R₄ = cyclohexyl-oxy-yl | 3.9796 |
| PGB-04 | 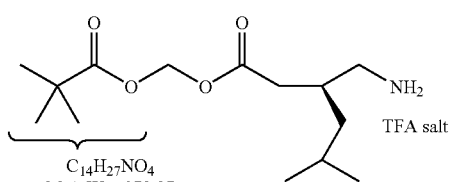 C₁₄H₂₇NO₄ Mol. Wt.: 273.37 TFA salt | Formula (II) 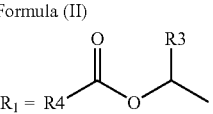 R₁ = R4 R₃ = hydrogen R₄ = isobutyl | 2.931 |
| PGB-05 | 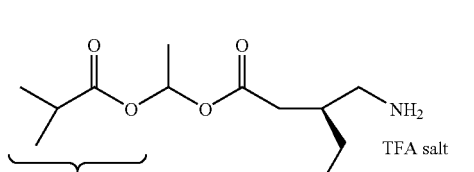 C₁₄H₂₇NO₄ Mol. Wt.: 273.37 TFA salt | Formula (II) 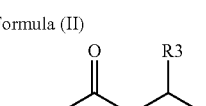 R₁ = R4 R₃ = methyl R₄ = isopropyl | 2.841 |
| PGB-06 | 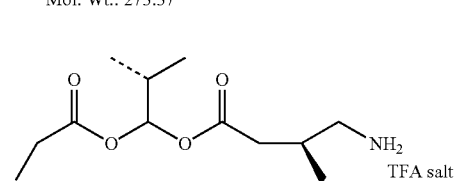 C₁₅H₂₉NO₄ Mol. Wt.: 287.40 TFA salt | Formula (II) 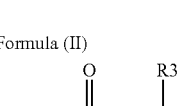 R₁ = R4 R₃ = isopropyl R₄ = ethyl | 3.46 |
| PGB-07 | 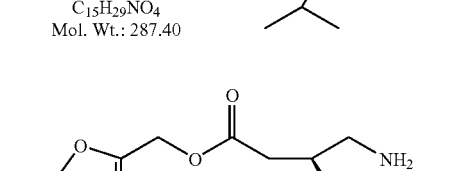 C₁₃H₂₁NO₅ Mol. Wt.: 271.31 HCl salt | Formula (II) 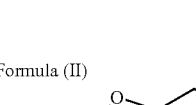 R₁ = R₂ = methyl | 1.018 |
| PGB-08 | 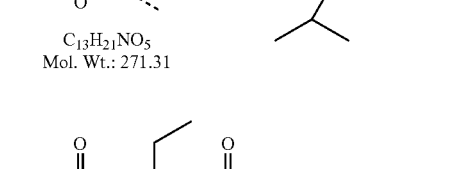 C₁₅H₂₉NO₄ Mol. Wt.: 287.40 TFA salt | Formula (II)  R₁ = R₁ = R4 R₃ = ethyl R₄ = isopropyl | 3.37 |

Example 3

Synthesis of PGB-02
(3-Aminomethyl-5-methyl-hexanoic acid 1-ethyloxycarbonyloxy-ethyl ester)

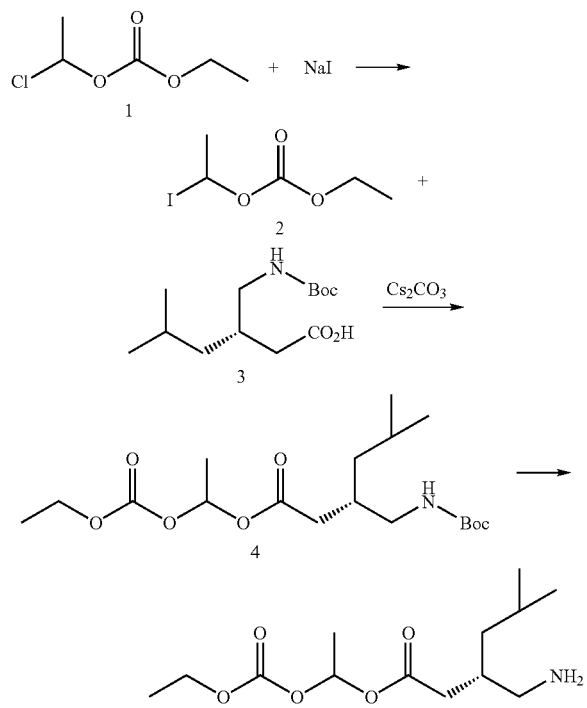

Procedure:

Sodium iodide (3.93 g, 26.2 mmol) was dissolved in anhydrous $CH_3CN$ (20 mL). Compound 1 (1.00 g, 6.55 mmol) in anhydrous $CH_3CN$ (8 mL) was added and stirred for 6 hours at 60° C. After filtering and concentration, the residue was diluted with ether and re-concentrated to give 1.04 g of Carbonic acid ethyl ester 1-iodo-ethyl ester 2 (Yield: 64%). $^1$HNMR (CDCl$_3$, 500 MHz) δ1.32 (t, J=7.0 Hz, 3H), 2.22 (d, J=6.0 Hz, 3H), 4.25 (q, J=7.0 Hz, 2H), 6.75 (q, J=6.0 Hz, 1H); $^{13}$CNMR (CDCl$_3$, 125 MHz) δ 14.14, 30.10, 52.34, 152.48.

Cesium carbonate $Cs_2CO_3$ (0.319 g, 1.82 mmol) was dissolved in methanol (7 mL) and S-form of compound 3 (0.924 g, 3.57 mmol) was added. The solution was stirred for 4 hours at room temperature, then filtered and concentrated to dryness. $CH_3CN$ (7 mL) and compound 2 (1.74 g, 7.04 mmol) were added and stirred overnight at room temperature. After filtration and concentrating, the residue was purified by chromatography on a column of silica gel (70-230 mesh, elution: EA/hexane=1:4) to give 0.815 g of slight brown oil 3-(tert-butoxycarbonylamino-methyl)-5-methyl-hexanoic acid 1-ethyloxycarbonyloxy-ethyl ester 4 (Yield: 23%). $^1$HNMR (CDCl$_3$, 500 MHz) δ 0.87~0.90 (m, 6H), 1.11~1.20 (m, 2H), 1.33 (t, J=7.0 Hz, 3H), 1.44 (s, 9H), 1.52 (d, J=5.5 Hz, 3H), 1.60~1.68 (m, 1H), 2.03~2.13 (m, 1H), 2.32~2.38 (m, 2H), 2.96~3.08 (m, 1H), 3.13~3.22 (m, 1H), 4.23 (q, J=7.0 Hz, 2H), 4.71~4.75 (m, 1H), 6.76 (q. J=5.5 Hz, 1H); $^{13}$CNMR (CDCl$_3$, 125 MHz) δ14.08, 19.50, 22.52, 22.62, 22.66, 22.72, 25.09, 28.35, 33.42, 33.61, 36.90, 37.10, 41.23, 41.25, 43.74, 43.81, 64.23, 79.12, 91.23, 153.05, 156.06, 171.01.

Trifluoroacetic acid (6.5 mL) was added to a solution of compound 4 (0.407 g, 1.08 mmol) and $CH_2Cl_2$ (2.85 mL) in an ice water bath, and the solution was maintained in the ice water bath for 30 minutes. The solution was warmed to room temperature and stirred for another 4.5 hours. The reaction solution was then concentrated and dried to give 0.50 g of 3-Aminomethyl-5-methyl-hexanoic acid 1-ethyloxycarbonyloxy-ethyl ester TFA salt 5 (Yield: 99%). $^1$HNMR (CDCl$_3$, 500 MHz) δ 0.87~0.91 (m, 6H), 1.23~1.39 (m, 6H), 1.51 (6rs, 3H), 1.61 (S, 1H), 2.20~2.38 (m, 1H), 2.40~2.61 (m, 2H), 2.98~3.21 (m, 2H), 4.2 (br s, 2H), 6.75 (br s 1H), 7.51~7.80 (br s, 2H), 9.35~9.80 (br s, 1H); $^{13}$C NMR (CDCl$_3$, 125 MHz) δ13.86, 13.87, 19.16, 19.19, 21.70, 21.74, 22.38, 22.40, 24.83, 30.95, 31.02, 36.48, 36.69, 41.07, 41.32, 44.25, 44.36, 64.82, 91.41, 91.45, 153.38, 153.40, 171.87, 172.08.

Example 4

Synthesis of PGB-03
(3-Aminomethyl-5-methyl-hexanoic acid 1-cyclohexyloxycarbonyloxy-ethyl ester)

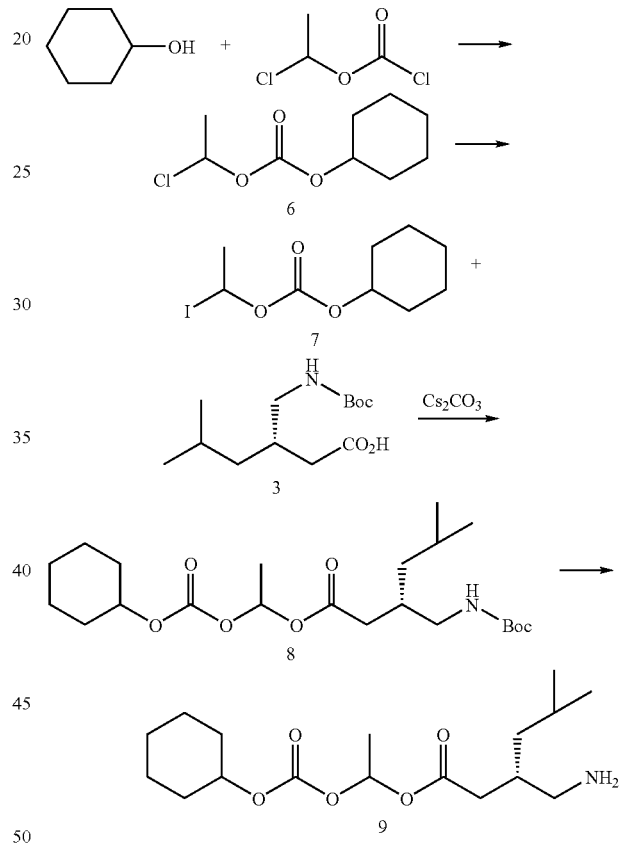

Procedure:

Cyclohexy alcohol (1.4 g, 13.97 mmol) was dissolved in $CH_2Cl_2$ (15 mL) under the treatment in a nitrogen atmosphere (0-5° C.). 1-Chloroethyl chloroformate (2.0 g, 13.97 mmol) and $CH_2Cl_2$ (10 mL) were slowly added. The solution was stirred for 15 minutes and pyridine (1.22 g, 15.42 mmol) and $CH_2Cl_2$ (2 mL) were added dropwise. After stirring overnight at room temperature, $CH_2Cl_2$ (20 mL) and water (20 mL) were added to the reaction solution. The product was extracted to the $CH_2Cl_2$ phase and washed with water (3×20 mL). The residue was dried and concentrated to give 2.64 g of Carbonic acid cyclohexyl ester 1-chloro-ethyl ester 6 (Yield: 94%). $^1$HNMR (CDCl$_3$, 500 MHz) δ 1.22-1.30 (m, 1H), 1.32-1.41 (m, 2H), 1.42-1.58 (m, 3H), 1.71-1.80 (m, 2H), 1.83 (d, J=6.0 Hz, 3H), 1.89-2.00 (m, 2H), 4.65-4.72 (m, 1H), 6.43 (q, J=6.0 Hz, 1H).

Sodium iodide (4.48 g, 29.88 mmol) was dissolved in anhydrous $CH_3CN$ (30 mL). Compound 6 (1.20 g, 5.98 mmol) and anhydrous $CH_3CN$ (3 mL) were added and stirred for 5.5 hours at 50° C. After filtering and concentration, the residue was diluted with ether and re-concentrated to give 1.21 g of carbonic acid cyclohexyl ester 1-iodo-ethyl ester 7 (Yield: 69%). $^1$HNMR (CDCl$_3$, 500 MHz) δ 1.25-1.40 (m, 3H), 1.41-1.58 (m, 3H), 1.70-1.78 (m, 2H), 1.85-1.95 (m, 2H), 2.22 (d, J=7.0 Hz, 3H), 4.66-4.71 (m, 1H), 6.77 (q, d=7.0 Hz, 1H).

Cesium carbonate $Cs_2CO_3$ (0.319 g, 0.98 mmol) was dissolved in methanol (5 mL) and S-form of compound 3 (0.5 g 1.28 mmol) was added. The solution was stirred for 4 hours at room temperature, then filtered and concentrated to dryness. $CH_3CN$ (5 mL) and compound 10 (1.0 g, 3.39 mmol) were added and the solution was stirred overnight at room temperature. After filtering and concentrating, the residue was purified by chromatography on a column of silica gel (70-230 mesh, elution: EA/hexane=1:4) to give 0.339 g of 3-(tert-butoxycarbonylamino-methyl)-5-methyl-hexanoic acid 1-cyclohexyl-oxycarbonyloxy-ethyl ester 8 (Yield: 23%). $^1$HNMR (CDCl$_3$, 500 MHz) δ0.87-0.90, (m, 6H), 1.10-1.21 (m, 2H), 1.25-1.42 (m, 3H), 2.04 (s, 9H), 1.55 (d, J=5.0 Hz, 3H), 1.41-1.56 (m, 3H), 1.60-1.64 (m, 1H), 1.72-1.78 (m, 2H), 1.88-1.92 (m, 2H), 2.04-2.15 (m, 1H), 2.23-2.34 (m, 2H), 2.95-3.08 (m, 1H), 3.11-3.23 (m, 1H), 4.61-4.75 (m, 2H), 6.75 (q, J=5.0 Hz, 1H); $^{13}$CNMR (CDCl$_3$, 125 MHz) δ14.17, 19.56, 20.99, 22.57, 22.64, 22.69, 22.74, 23.56, 25.15, 28.38, 31.38, 31.39, 33.53, 33.73, 37.01, 37.16, 41.28, 41.32, 43.86, 60.35, 77.44, 79.13, 91.18, 91.19, 152.55, 156.07, 170.97.

Compound 8 (0.172 g, 0.40 mmol) was added to $CH_2Cl_2$ (2.85 mL) in an ice water bath. Trifluoroacetic acid (2.85 mL) was then added and maintained in the ice water bath for 30 minutes. The solution was warmed to room temperature and stirred for 5 hours. The reaction solution was then concentrated and dried to give 0.165 g of 3-aminomethyl-5-methyl-hexanoic acid 1-cyclohexyloxycarbonyloxy-ethyl ester TFA salt 9 (Yield: 93%). $^1$HNMR (CDCl$_3$, 500 MHz) δ0.87-0.91 (m, 6H), 1.21-1.40 (m, 6H), 1.41-1.56 (m, 6H), 1.60-1.63 (m, 1H), 1.70-1.78 (m, 2H), 1.82-1.93 (m, 2H), 2.23-2.64 (m, 3H), 3.01-3.31 (m, 2H), 4.58-4.63 (br s, 1H), 6.77 (br s, 1H), 8.00 (br s, 2H); $^{13}$CNMR (CDCl$_3$, 125 MHz) δ19.01, 21.52, 21.58, 22.19, 23.16, 24.67, 24.82, 30.89, 31.03, 36.68, 36.87, 41.07, 41.30, 44.20, 65.51, 77.76, 91.32, 91.36, 152.63, 152.69, 172.02, 172.08; LC/MS:ESI positive mode (M+H): 330.36.

Example 5

Synthesis of PGB-04
(3-Aminomethyl-5-methyl-hexanoic acid
2,2-dimethyl-propionyloxymethyl ester)

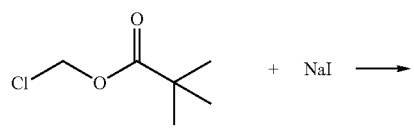

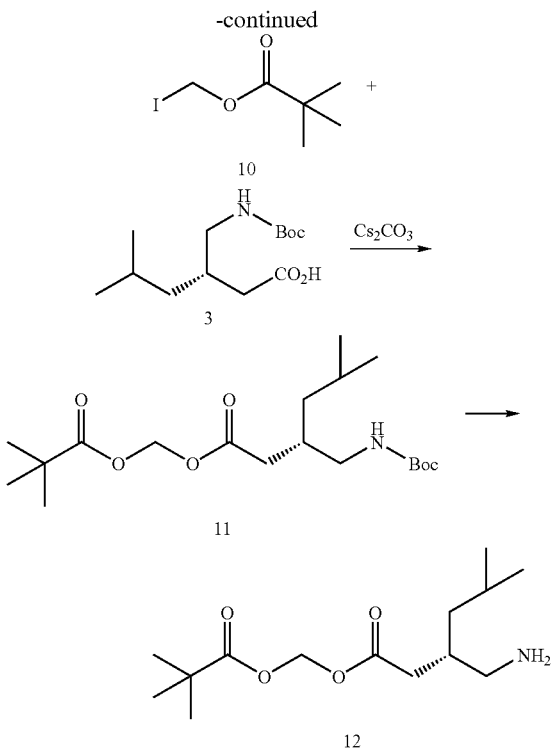

Procedure:

Sodium iodide (2.5 g, 16.35 mmol) was dissolved in acetone (13 mL). Chloromethyl tert-butyl ester (1.0 g, 6.64 mmol) and acetone (2 mL) were added and stirred for 5.5 hours at 50~55° C. in a nitrogen atmosphere. After filtration and concentration, the reaction solution was diluted with ether (10 mL) and then re-concentrated to give 1.354 g of brown liquid 2,2-dimethyl-propionic acid iodomethyl ester 10 (Yield: 83%). $^1$HNMR (CDCl$_3$, 500 MHz) δ 1.19 (s, 9H), 5.93 (s, 2H).

Cesium carbonate (0.344 g, 1.05 mmol) was dissolved in methanol (5 mL) and S-form of compound 3 (0.50 g 1.28 mmol) was added. The solution was stirred for 4 hours at room temperature, then filtered and concentrated to dryness. The product was dissolved in $CH_3CN$ (5 mL). The solution of compound 10 (0.948 g, 3.87 mmol) and $CH_3CN$ (5 mL) were then added and stirred overnight at room temperature. After filtration and concentrating, the residue was purified by chromatography on a column of silica gel (70-230 mesh, elution: EA/hexane=1:4) to give 0.689 g of viscous liquid 3-(tert-butoxycarbonylamino-methyl)-5-methyl-hexanoic acid 2,2-dimethyl-propionyloxymethyl ester 11 (Yield: 95%). $^1$HNMR (CDCl$_3$, 500 MHz) δ2.87-0.91 (m, 6H), 1.06-1.23 (m, 2H), 1.19 (S, 9H), 1.43 (S, 9H), 1.63-1.68 (m, 2H), 2.12-2.17 (m, 1H), 2.30-2.38 (m, 2H), 2.96-3.06 (m, 1H), 3.16-3.22 (m, 1H), 4.62-4.70 (m, 1H), 5.73, 5.76 (dd, J=4.5, 9.0 Hz, 2H); $^{13}$CNMR (CDCl$_3$, 125 MHz) δ 14.16, 22.59, 22.69, 25.15, 26.85, 28.37, 33.63, 36.95, 38.74, 41.29, 43.82, 60.58, 79.20, 79.57, 156.05, 171.67, 177.12.

Compound 11 (0.345 g) was dissolved in $CH_2Cl_2$ (6 mL). Trifluoroacetic acid (2.85 mL) was slowly added in an ice water bath and maintained for 30 minutes. The solution was warmed to room temperature and stirred for 4.5 hours. After concentrating and diluting with ether, 0.220 g of white to slightly yellow solid 3-aminomethyl-5-methyl-hexanoic acid 2,2-dimethyl-propionyloxymethyl ester TFA salt 12, was obtained (Yield: 93%). ¹HNMR (CDCl₃, 500 MHz) δ0.98-1.00 (m, 6H), 1.26 (s, 9H), 1.32 (t, J=7.5, 2H), 1.70-1.79 (m, 1H), 2.28-2.35 (m, 1H), 2.53-3.02 (m, 2H), 3.03 (d, J=8.0 Hz, 2H), 3.07 (s, 2H), 5.82, 5.84 (dd, J=2.0, 7.0 Hz, 2H); ¹³CNMR (CDCl₃, 125 MHz) δ21.86, 22.43, 24.92, 26.73, 27.02, 31.18, 36.23, 38.76, 41.05, 43.84, 79.84, 171.94, 177.44. LC/MS: ESI positive mode (M+H): 274.30.

Example 6

Synthesis of PGB-05
(3-Aminomethyl-5-methyl-hexanoic acid 1-isobutyryloxy-ethyl ester)

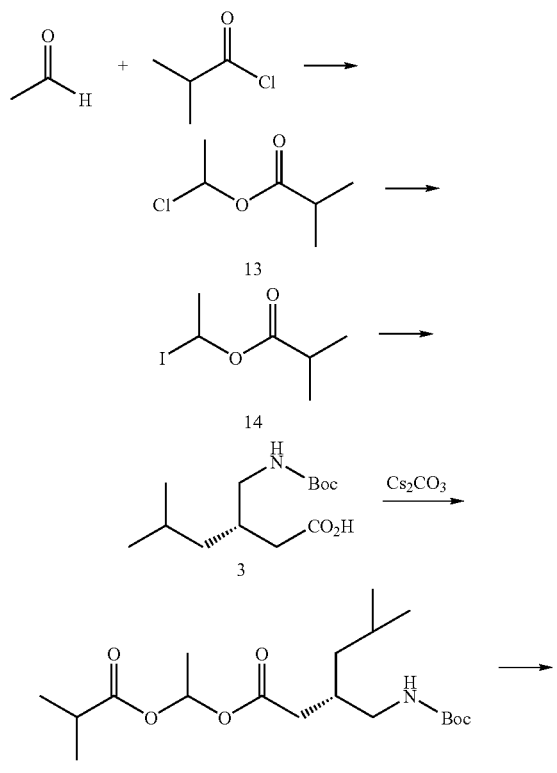

Procedure:
Acetaldehyde (2.40 g, 54.5 mmol) was added to isobutyryl chloride (5.94 g, 55.7 mmol) in a nitrogen atmosphere (0-5° C.) and maintained for 30 minutes at 0-5° C. After stirring for 4 hours at room temperature, the reaction solution was distilled at 35-40° C. under vacuum (4 torr) to give 1.91 g of colorless liquid isobutyric acid 1-chloro-ethyl ester 13 (Yield: 23%). ¹HNMR (CDCl₃, 500 MHz) δ1.19 (t, J=6.0 Hz, 6H), 1.79 (d, J=5.5 Hz, 3H), 2.55-2.60 (m, 1H), 6.54 (q, J=5.5 Hz, 1H); ¹³CNMR (CDCl₃, 125 MHz) δ 18.14, 18.22, 24.85, 33.55, 80.41, 171.31.

Sodium iodide (4.5 g, 29.43 mmol) was dissolved in CH₃CN (13 mL). Compound 13 (2.16 g, 14.4 mmol) and CH₃CN (5 mL) were added and stirred for 6.5 hours. After filtering and concentrating, the reaction solution was diluted with ether (10 mL) and then re-concentrated to give 1.597 g of isobutyric acid 1-iodo-ethyl ester 14 (Yield: 46%). ¹HNMR (CDCl₃, 500 MHz) δ1.16-1.21 (m, 6H), 2.20 (d, J=5.5 Hz, 3H), 2.45-2.61 (m, 1H), 6.86 (q, J=6.0 Hz, 1H).

Cesium carbonate (0.365 g, 1.12 mmol) was dissolved in methanol (5 mL) and S-form of compound 4 (0.500 g, 1.28 mmol) was added. The solution was stirred for 4 hours at room temperature and concentrated to dryness. The residue was diluted with CH₃CN (7.5 mL), and compound 14 (0.945 g, 3.56 mmol) and CH₃CN (5 mL) were then added. After stirring overnight at room temperature, the reaction solution was filtered and concentrated to give 1 g of the crude product, which was then purified by chromatography on a column of silica gel (70-230 mesh, elution: EA/Hexane=1:4). Compound 3-(tert-butoxycarbonylamino-methyl)-5-methyl-hexanoic acid 1-isobutyryloxy-ethyl ester 15 (0.13 g) was obtained with 27% yield. ¹HNMR (CDCl₃, 500 MHz) δ0.87-0.92 (m, 6H), 1.10-1.21 (m, 2H), 1.55 (d, J=5 Hz, 6H), 1.44 (s, 9H), 1.48 (d, J=5.5 Hz, 3H), 1.52-1.59 (m, 2H), 2.06-2.12 (m, 1H), 2.28-2.35 (m, 2H), 2.49-2.57 (m, 1H), 2.93-3.06 (m, 1H), 3.12-3.22 (m, 1H), 4.62-4.73 (m, 1H), 6.84 (q, J=5.5 Hz, 1H).

Compound 15 (0.13 g, 0.35 mmol) was dissolved in CH₂Cl₂ (2.5 mL). Trifouoroacetic acid (1.83 mL) was added in an ice water bath and maintained for 1 hour. The solution was then warmed to room temperature and stirred for 5 hours. After concentrating and drying, 3-aminomethyl-5-methyl-hexanoic acid 1-isobutyryloxy-ethyl ester TFA salt 16 (0.12 g) was obtained with 62% yield. ¹HNMR (CDCl₃, 500 MHz) δ0.87-0.91 (m, 6H), 1.14-1.16 (m, 6H), 1.21-1.29 (m, 2H), 1.46-1.48 (m, 3H), 1.51-1.63 (m, 1H), 2.20-2.33 (m, 1H), 2.39-2.46 (m, 1H), 2.50-2.60 (m, 2H), 2.96-3.06 (m, 1H), 3.08-3.10 (m, 1H), 5.67 (br s, 2H), 6.83 (br s, 1H); ¹³CNMR (CDCl₃, 125 MHz) δ 18.44, 18.46, 19.16, 19.19, 21.82, 22.46, 24.93, 31.09, 31.14, 33.82, 33.84, 36.75, 37.02, 41.23, 41.51, 44.40, 44.57, 88.82, 88.90, 172.11, 172.21, 175.96. LC/MS:ESI positive mode (M+H): 274.30.

Example 7

Synthesis of PGB-06 (3-Aminomethyl-5-methyl-hexanoic acid 2-methyl-1-propionyloxy-propyl ester)

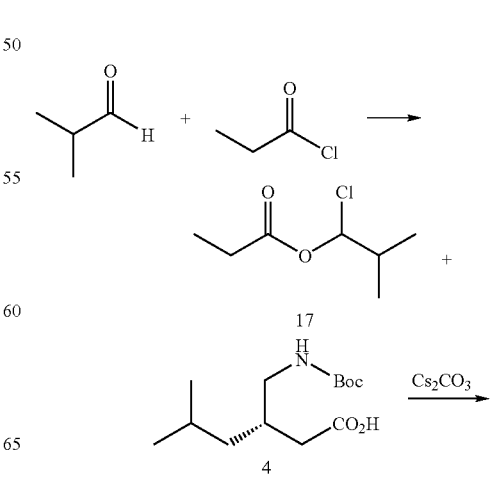

-continued

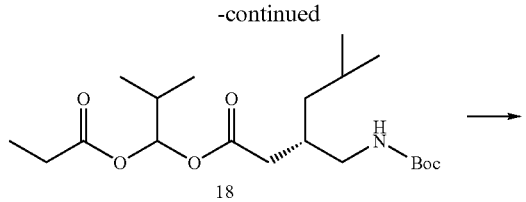

18

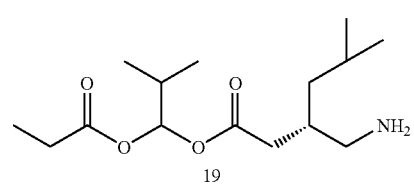

19

Procedure:

Isobutylaldehyde (3 g, 41.6 mmol) was added to propionyl chloride (3.85 g, 41.6 mmol) in a nitrogen atmosphere at 0-5° C. and stirred for 4 hours. The solution was distilled in vacuum at 50° C. and 2.59 g of colorless liquid propionic acid 1-chloro-2-methyl-propyl ester 17 was obtained (Yield: 38%). $^1$HNMR (CDCl$_3$, 500 MHz) δ1.06 (t, J=7.0 Hz, 6H), 7.60 (t, J=7.5 Hz, 3H), 2.13-2.17 (m, 1H), 2.39 (q, J=7.5 Hz, 2H), 6.31 (d, J=4.5 Hz, 1H); $^{13}$CNMR (CDCl$_3$, 125 MHz) δ8.66, 17.25, 17.36, 27.49, 35.19, 88.61, 172.16.

Cesium carbonate (0.348 g, 1.07 mmol) was dissolved in methanol (5 mL) and S-form of compound 3 (0.5 g, 1.28 mmol) was added. The solution was stirred for 4 hours at room temperature and concentrated to dryness. A solution of propionic acid 1-chloro-2-methyl-propyl ester (0.68 g, 4.13 mmol) in DMF (3 mL) was added and stirred for 5 hours at 50° C. After filtering, the filtrate was extracted with EtOAc and water three times. The organic layer was concentrated and the crude product was purified by column chromatography (silica gel 70-230 mesh, eluent: EA/Hexane=1/4). The slightly yellow viscous liquid 3-(tert-butoxycarbonylamino-methyl)-5-methyl-hexanoic acid 2-methyl-1-propionyloxy-propyl ester 18 (0.196 g) was obtained (Yield: 40%). $^1$HNMR (CDCl$_3$, 500 MHz) δ0.86-0.94 (m, 9H), 0.96 (d, J=7.0 Hz, 3H), 1.10-1.22 (m, 3H), 1.44 (s, 9H), 1.56-1.60 (m, 1H), 1.61-1.70 (m, 1H), 1.98-2.14 (m, 2H), 2.31 (q, J=7.0 Hz, 1H), 2.35 (q, J=7.5 Hz, 1H), 2.96-3.06 (m, 1H), 3.16-3.25 (m, 1H), 4.26-4.71 (m, 1H), 6.65 (d, J=5.5 Hz, 1H).

Compound 18 (0.196 g, 0.51 mmol) was dissolved in CH$_2$Cl$_2$ (2 mL). Trifluoroacetic acid (3.25 mL) was added in an ice water bath and maintained for 30 minutes. The solution was then warmed to room temperature and stirred for 5 hours. After concentrating and drying, 3-aminomethyl-5-methyl-hexanoic acid 2-methyl-1-propionyloxy-propyl ester TFA salt 19 (0.194 g) was obtained with a yield of 95%. $^1$HNMR (CD$_3$OD, 500 MHz) δ0.88-0.92 (m, 6H), 0.94 (d, J=6.5 Hz, 3H), 1.08 (t, J=7.5 Hz, 2H), 1.20-1.28 (m, 2H), 1.60-1.69 (m, 1H), 1.95-2.02 (m, 1H), 2.16-2.23 (m, 1H), 2.29-2.46 (m, 3H), 2.89-2.98 (m, 2H), 3.27 (s, 1H), 6.59 (d, J=5 Hz, 1H); $^{13}$CNMR (CDCl$_3$, 125 MHz) δ9.29, 9.31, 16.74, 16.84, 16.86, 22.58, 22.59, 23.25, 23.27, 23.31, 26.28, 26.32, 28.28, 32.83, 32.90, 32.95, 36.85, 36.93, 37.28, 41.80, 41.89, 42.24, 44.31, 44.34, 44.71, 49.66, 94.54, 94.57, 172.16, 172.18, 174.46. LC/MS: ESI positive mode (M+H): 288.30.

Example 8

Synthesis of PGB-07 (3-Aminomethyl-5-methyl-hexanoic acid 5-methyl-2-oxo-[1,3]dioxol-4-ylmethyl ester)

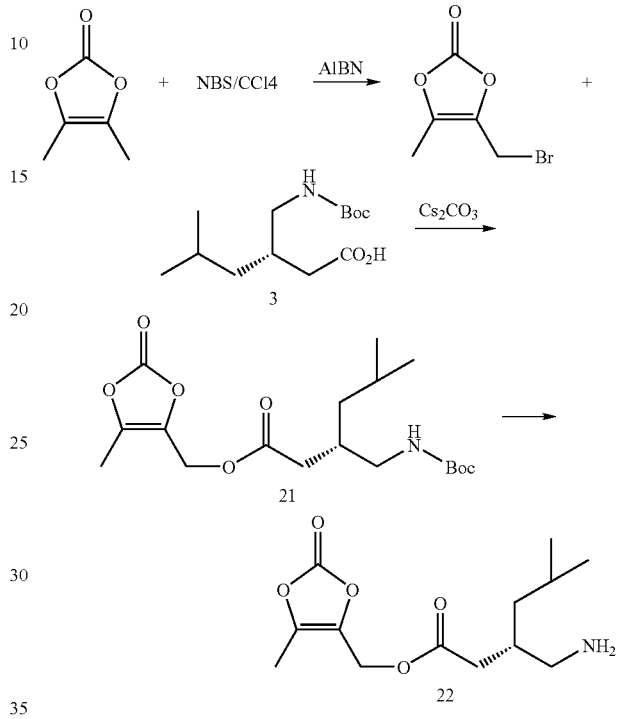

Procedure:

Compound 20 was prepared following the steps disclosed in the literature (Sakamoto et al., Chem. Pharm. Bull, 1984, 32, 2241).

Cesium carbonate (0.20 g, 0.61 mmol) was dissolved in methanol and S-form of compound 3 (0.32 g) was added. After stirring for 2 hours at room temperature, the solvent was removed under reduced pressure. The residue was diluted with N,N-dimethylacetamide ("DMA", 3.8 mL), where a solution of compound 20 (0.2 g, 0.032 mmol) in DMA (1 mL) was added. After stirring overnight, the reaction solution was diluted with water (50 mL), extracted with EtOAc, washed with brine, dried over MgSO$_4$, and then concentrated under reduced pressure. The oil crude product (0.63 g) was purified by chromatography on a column of silica gel (70-230 mesh, elution: EA/Hexane=1/3) to give 0.33 g of 3-(tert-butoxycarbonylamino-methyl)-5-methyl-hexanoic acid 5-methyl-2-oxo-[1,3]dioxol-4-ylmethyl ester 21 (Yield: 72%). $^1$HNMR (CDCl$_3$, 500 MHz) δ 0.87-0.91 (m, 6H), 1.07-1.15 (m, 1H), 1.16-1.21 (m, 1H), 1.43 (s, 9H), 1.59-1.67 (m, 1H), 2.09-2.12 (m, 1H), 2.18 (s, 3H), 2.23-2.36 (m, 2H), 2.96-3.03 (m, 1H), 3.17-3.23 (m, 1H), 4.68 (br s, 1H), 4.85 (s, 2H). $^{13}$CNMR (CDCl$_3$, 125 MHz) δ 9.25, 22.57, 22.60, 25.13, 28.29, 29.59, 33.62, 6.2, 4.38, 43.79, 53.56, 79.7, 13.51, 13.9, 152.00, 5.02, 172.38.

Compound 21 (150 mg) was dissolved in CH$_2$Cl$_2$ (2.5 mL) with stirring. A solution of 4M HCl/dioxane (2 mL) was added and stirred for 5 hours at room temperature. After the removal of the solvent under reduced pressure, 110 mg of slightly yellow liquid 3-aminomethyl-5-methyl-hexanoic acid 5-methyl-2-oxo-[1,3]dioxol-4-ylmethyl ester HCl salt 22 was obtained (Yield 89%). $^1$HNMR (CDCl$_3$, 500 MHz) δ 0.88-0.92 (m, 6H), 1.18-1.29 (m, 1H), 1.31-1.40 (m, 1H), 1.58-1.68 (m, 1H), 2.19 (s, 3H), 2.37 (br s, 1H), 2.50-2.69 (m, 2H), 3.01-3.18 (m, 2H), 4.89 (s, 2H), 8.22 (br s, 2H); $^{13}$CNMR (CDCl$_3$, 125 MHz) δ 9.34, 22.38, 22.46, 25.04, 29.61, 31.21, 36.02, 40.92, 42.98, 53.99, 133.34, 140.21, 152.14, 171.76. LC/MS:ESI positive mode (M+H): 272.20.

Example 9

Synthesis of PGB-08
(3-Aminomethyl-5-methyl-hexanoic acid 1-isobutyryloxy-propyl ester)

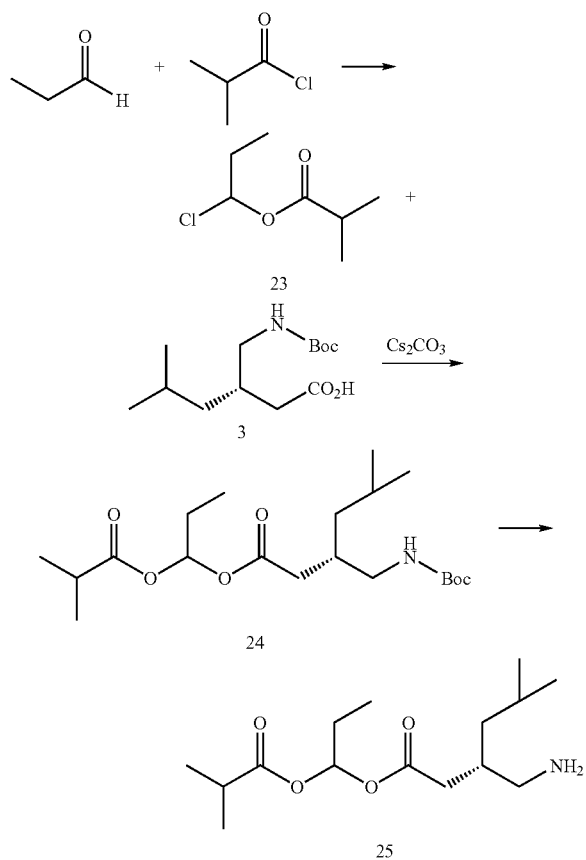

Procedure:

Propionaldehyde (1.60 g, 27.5 mmol) and isobutyrl chloride (3.0 g, 27.5 mmol) was mixed and stirred for 4 hours at 50° C. The reaction solution was diluted with CH$_2$Cl$_2$ (15 mL) and washed with saturated NaHCO$_3$ (2×15 mL) and water. After removing the solvent under reduced pressure, the residue was distilled under 4 torr of vacuum at 40-45° C. to give 1.22 g of colorless liquid isobutyric acid 1-chloro-propyl ester 23 (Yield: 27%). $^1$HNMR (CDCl$_3$, 500 MHz) δ1.06 (t, J=7.5 Hz, 3H), 1.20-1.22 (m, 6H), 2.04-2.07 (m, 2H), 2.59-2.63 (m, 1H), 6.40 (t, J=5.5 Hz, 1H).

Cesium carbonate (0.5 g, 1.53 mmol) was dissolved in methanol (8 mL) and S-form of Compound 3 (0.8 g, 2.04 mmol) was added. After stirring for 75 minutes at room temperature, a solution of liquid compound 23 (1.1 g, 6.68 mmol) in DMF (6.5 mL) was added, and stirred for 5 hours at 50° C. The reaction solution was filtered. The filtered solution was diluted with EA (25 mL) and washed with water (3×25 mL). After concentrating and drying, the collected crude product (1.39 g) was then purified by chromatography on a column of silica gel (70-230 mesh, elution: EA/Hexane=1/3) to give 0.71 g of 3-(tert-butoxycarbonylamino-methyl)-5-methyl-hexanoic acid 1-isobutyryloxy-propyl ester 24 (Yield: 89%). $^1$HNMR (CDCl$_3$, 500 MHz) δ0.87-0.95 (m, 6H), 0.98 (t, J=5.0 Hz, 3H), 1.15-1.21 (m, 8H), 1.26 (s, 9H), 1.61-1.69 (m, 1H), 1.78-1.82 (m, 2H), 2.06-2.13 (m, 1H), 2.22-2.35 (m, 2H), 2.51-2.60 (m, 1H), 2.90-3.05 (m, 1H), 3.16-3.23 (m, 1H), 4.63-4.73 (br s, 1H), 6.73 (t, J=5.5 Hz, 1H); $^{13}$CNMR (CDCl$_3$, 125 MHz) δ7.58, 7.60, 18.65, 18.68, 22.56, 22.59, 22.68, 25.12, 26.39, 28.35, 33.52, 33.68, 33.86, 36.98, 37.12, 41.24, 43.87, 79.09, 91.24, 156.07, 171.11, 175.09.

Compound 24 (0.3 g, 0.77 mmol) was dissolved in CH$_2$Cl$_2$ (5 mL) and TFA (4.5 mL) was added and maintained in an ice water bath for 30 minutes. The solution was then warmed to room temperature and stirred for 5 hours. After concentrating and drying, 0.25 g of 3-aminomethyl-5-methyl-hexanoic acid 1-isobutyryloxy-propyl ester TFA salt 25 was obtained (Yield: 80%). $^1$HNMR (CDCl$_3$, 500 MHz) δ0.87-0.95 (m, 6H), 1.15-1.65 (m, 4H), 1.18-1.28 (m, 2H), 1.52-1.67 (m, 1H), 1.71-1.82 (m, 2H), 2.18-2.31 (m, 1H), 2.39-2.46 (m, 1H), 2.51-2.62 (m, 2H), 3.02 (br s, 1H), 3.19 (br s, 1H), 6.89 (t, J=5.5 Hz, 1H), 7.48 (br s, 2H); $^{13}$CNMR (CDCl$_3$, 125 MHz) δ 7.29, 7.35, 14.69, 18.39, 18.42, 18.48, 18.52, 21.70, 21.73, 22.43, 24.90, 26.18, 31.05, 31.13, 33.93, 36.92, 37.08, 41.26, 41.47, 44.73, 44.79, 66.05, 91.73, 91.83, 172.58, 172.69, 176.43.

Example 10

In Vivo Pharmacokinetic Study

PGB-03, PGB-05, PGB-06, PGB-07 and pregabalin were dissolved in 2% Tween 80 to achieve concentrations of 1.25, 3.45, 30.5, 31.5 and 2.4 mg/ml.

Male Sprague-Dawley rats (280-320 g, 3 rats/group) received the following treatments by oral gavage: PGB-03, PGB-05, PGB-06, PGB-07 and pregabalin, at 34.5, 30.5, 31.5, 24 and 12.5 mg/kg (equivalent to 12.5 mg/kg of pregabalin). The blood samples were obtained at 0, 0.25, 0.5, 0.75, 1, 2, 5, 8, 12 and 24 hours after the treatment and processed immediately for 50/50 acetonitrile/methanol (V/V) at 4° C. All plasma samples were subsequently analyzed for test compounds and pregabalin using LC/MS/MS.

Results:

The concentration of test compounds in blood after oral administration of all test compounds is detected at any timepoint. Table 2 shows data calculated for bioavailability, $C_{max}$ ratio and $T_{max}$ of pregabalin after administration of test compounds. As Table 2 shows, bioavailability and $C_{max}$ ratio are 56.6% and 0.785 respectively after administration of PGB-03, 62.7% and 0.625 respectively after administration of PGB-05, 62.4% and 0.666 respectively after administration of PGB-06, and 75.8% and 0.905 respectively after administration of PGB-07. The results show that the test compounds could be converted to pregabalin prior to entering the systemic circulation, and that they thus behaved as prodrugs of pregabalin in vivo.

TABLE 2

| | Pregabalin AUC₀₋ (ng/ml × h) | BA (%) | $C_{max}$ (ng/ml) | $C_{max}$ ratio | $T_{max}$ (h) |
|---|---|---|---|---|---|
| Pregabalin | 168421.1 | 100 | 27420.5 | 1 | 0.92 |
| PGB-03 | 95361.0 | 56.6 | 21529.0 | 0.785 | 0.50 |
| PGB-05 | 105656.0 | 62.7 | 17147.3 | 0.625 | 0.58 |
| PGB-06 | 105128.5 | 62.4 | 18096.1 | 0.666 | 1.00 |
| PGB-07 | 127588.6 | 75.8 | 24826.6 | 0.905 | 1.25 |

BA (%): pregabalin AUC of test groups/pregabalin AUC of pregabalin group.
$C_{max}$ ratio: $C_{max}$ of test groups/$C_{max}$ of pregabalin group.

The above examples are illustrative and non-limiting examples of the invention. A skilled person would know how to modify the examples in order to obtain other compounds of the invention. For instance, compound 3 in the synthesis process of the examples can be easily replaced by

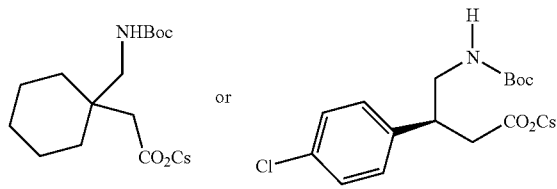

to obtain compounds of formula (III) or formula (IV) of the invention. Thus, other embodiments are also included in the scope of the invention.

What is claimed is:

1. A compound of formula (I):

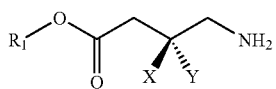

or a pharmaceutically acceptable salt, hydrate or solvate thereof;
wherein
R₁ is

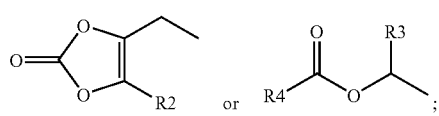

R₂ and R₃ are independently hydrogen or alkyl;
R₄ is $C_1$-$C_6$ alkyl group, $C_6$-$C_8$ aryl group or $C_1$-$C_6$ alkoxyl group; and
X and Y are independently hydrogen, chlorophenyl, or 2-methylpropyl, or benzyl, or optionally X and Y together with the carbon atom to which they are bonded form a cyclohexyl.

2. The compound according to claim 1, wherein the compound of formula (I) is a compound of formula (II):

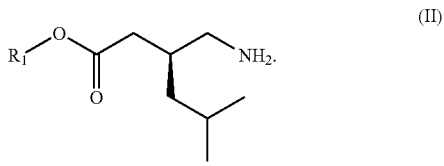

3. The compound according to claim 1, wherein the compound of formula (I) is a compound of formula (III):

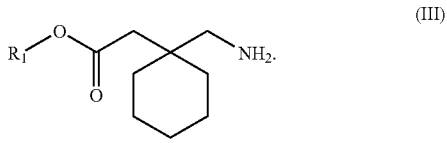

4. The compound according to claim 1, wherein the compound of formula (I) is a compound of formula (IV):

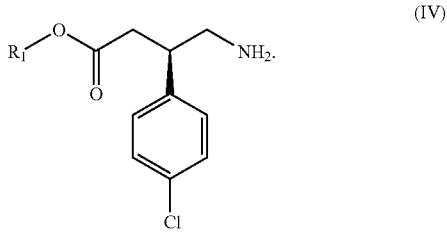

5. The compound according to claim 2, wherein the compound is a compound of formula (V):

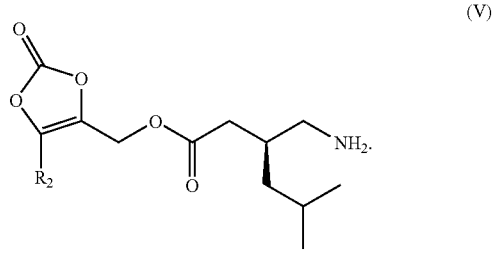

6. The compound according to claim 5, wherein R₂ is methyl.

7. The compound according to claim 2, wherein the compound is a compound of formula (VI):

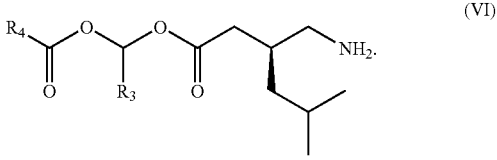

8. The compound according to claim 7, wherein R₄ is $C_1$-$C_6$ alkoxyl group.

9. The compound according to claim 8, wherein $R_4$ is ethoxyl or cyclohexyloxy-yl.

10. The compound according to claim 7, wherein $R_4$ is $C_1$-$C_6$ alkyl group.

11. The compound according to claim 7, wherein $R_4$ is isobutyl, isopropyl or ethyl.

12. The compound according to claim 7, wherein $R_3$ is hydrogen, methyl, ethyl or isopropyl.

13. The compound according to claim 2, wherein the compound is selected from the group consisting of:
   3-Aminomethyl-5-methyl-hexanoic acid 1-ethyloxycarbonyloxy-ethyl ester,
   3-Aminomethyl-5-methyl-hexanoic acid 1-cyclohexyloxycarbonyloxy-ethyl ester,
   3-Aminomethyl-5-methyl-hexanoic acid 2,2-dimethyl-propionyloxymethyl ester,
   3-Aminomethyl-5-methyl-hexanoic acid 1-isobutyryloxy-ethyl ester,
   3-Aminomethyl-5-methyl-hexanoic acid 2-methyl-1-propionyloxy-propyl ester,
   3-Aminomethyl-5-methyl-hexanoic acid 5-methyl-2-oxo-[1,3]dioxol-4-ylmethyl ester, and
   3-Aminomethyl-5-methyl-hexanoic acid 1-isobutyryloxy-propyl ester.

14. A pharmaceutical composition comprising a compound according to claim 1 and a pharmaceutically acceptable carrier.

15. A pharmaceutical composition comprising a compound according to claim 13 or a salt thereof and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,879,906 B2 |
| APPLICATION NO. | : 11/943983 |
| DATED | : February 1, 2011 |
| INVENTOR(S) | : Hwang et al. |

It is certified that error appears in the above-identified patent and that said Letters Patent is hereby corrected as shown below:

In the specification Column 3, line 43, please delete "hexylene" and replace it with --hexalene--.

Signed and Sealed this
Twenty-fourth Day of April, 2012

David J. Kappos
*Director of the United States Patent and Trademark Office*